(12) United States Patent
Miller et al.

(10) Patent No.: US 6,573,041 B2
(45) Date of Patent: Jun. 3, 2003

(54) NEURONAL CELL MODEL AND METHODS OF USE THEREOF

(75) Inventors: Craig S. Miller, Nicholasville, KY (US); Robert J. Jacob, Lexington, KY (US); Robert J. Danaher, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/984,337

(22) Filed: Oct. 29, 2001

(65) Prior Publication Data

US 2003/0032006 A1 Feb. 13, 2003

Related U.S. Application Data

(60) Provisional application No. 60/243,701, filed on Oct. 27, 2000.

(51) Int. Cl.$^7$ .............................. C12Q 1/70; C12N 5/10
(52) U.S. Cl. ............................... 435/5; 435/6; 435/353; 435/235.1
(58) Field of Search ............................... 435/5, 6, 353, 435/235.1

(56) References Cited

U.S. PATENT DOCUMENTS 6,268,124 B1 * 7/2001 Miller et al. .................... 435/5

OTHER PUBLICATIONS

Wang et al. Journal of Virology 69 (5): 2873–2880, 1995.*
Danaher et al. Journal of neurovirology Aug. 1999, 5 (4) p374–83 (abstract only cited).*
Danaher et al. Journal of neurovirology Jun. 1999, 5 (3) p258–67 (abstract only cited).*
Al–Saadi SA, Gross P, Wildy P (1988). Herpes simplex virus type 2 latency in the footpad of mice: effect of acycloguanosine on the recovery of virus. *J Gen Virol* 69: 433–438.
Benedetti J, Corey L, Ashley R (1994). Recurrence rates in genital herpes after symptomatic first–episode infection. *Ann Intern Med* 121: 847–854.
Bourne N, Stanberry LR. Connelly BL, Kurawadwala J, Straus SE, Krause PR (1994). Quantity of latency–associated transcript produced by herpes simplex virus is not predictive of the frequency of experimental recurrent genital herpes. *J Infect Dis* 169: 1084–1087.
Colberg–Poley AM, Isom HC, Rapp F (1979). Reactivation of herpes simplex virus type 2 from a quiescent state by human cytomegalovirus. *Proc Nat Acad Sci* USA 76: 5948–5951.
Colberg–Poley AM, Isom HC, Rapp F (1981). Involvement of an early human cytomegalovirus function in reactivation of quiescent herpes simplex virus type 2. *J Virol* 37: 1051–1059.

Croen KD, Ostrove JM, Dragovic L, Straus E (1991). Characterization of herpes simplex virus type 2 latency–associated transcription in human sacral ganglia and in cell culture. *J Infect Dis* 163: 23–28.
Danaher RJ, Jacob RJ, Miller CS (1999a). Establishment of a quiescent herpes simplex virus type 1 infection in neurally–differentiated PC12 cells. *J NeuroVirol* 5: 258–267.
Danaher RJ, Jacob RJ, Chorak MD, Freeman CS, Miller CS (1999b). Heat stress induces reactivation of herpes simplex virus type 1 from quiescently infected neurally–differentiated PC12 cells. *J NeuroVirol* 5: 374–383.
Harris RA, Everett RD, Zhu X, Silverstein S, Preston CM. (1989). The HSV immediate early protein VMV 110 reactivates latent HSV type 2 in an in vitro latency system. *J Virol* 63: 3513–3515.
Kondo Y, Yura Y, Iga H, Yanagawa T, Yoshida H. Furumoto N, Sato M (1990). Effect of hexamethylene biscatamide and cyclosporin A on recovery of herpes simplex virus type 2 from the in vitro model of latency in a human neuroblastoma cell line. *Cancer Res* 50: 7852–7857.
Krause PR, Stanberry LR, Bourne N, Connelly B, Kurawadwala JF, Patel A, Straus SE (1995). Expression of the herpes simplex virus type 2 latency–associated transcript enhances spontaneous reactivation of genital herpes in latently infected guinea pigs. *J Exp Med* 181: 297–306.
Kurata T, Kurata K, Aoyama K (1978). Reactivation of herpes simplex virus (type 2) infection in trigeminal ganglia and oral lips with cyclophosphamide treatment. *Jpn J Exp Med* 48: 427–435.
MacLean A, Robertson L, McKay E, Brown SM (1991). The RL neurovirulence locus in herpes simplex virus type 2 strain HG52 plays no role in latency. *J Gen Virol* 72: 2305–2310.

(List continued on next page.)

Primary Examiner—Mary E. Mosher
(74) Attorney, Agent, or Firm—McDermott, Will & Emery

(57) ABSTRACT

We previously described a novel in vitro model of a non-productive herpes simplex virus type 1 (HSV-1) infection in neurally-differentiated (ND)-PC12 cells that allows for inducible virus replication upon forskolin and heat stress (HS) treatment. In this research, we further characterized the model with respect to HSV-2 strain 333. We found that: (i) ND-PC12 cells are non-permissive to HSV-2 replication; (ii) HSV-2 can establish a quiescent infection, like HSV-1, in ND-PC12 cells with the transient use of acycloguanosine (ACV); however unlike HSV-1, anti-viral conditions are not obligatory to establish and maintain a quiescent state; (iii) the quiescent state is maintained in the presence of Vero cell cocultivation indicating that such cultures are free of infectious virus; and (iv) a high percentage of quiescently infected (QIF)-PC 12 cell cultures (80–100%) produce HSV-2 in response to forskolin and HS (43° C., 3 h) treatment for as long as 4 weeks post infection. These findings indicate that ND-PC12 cells can harbor HSV-2 in a cryptic and non-productive state that is reversible. This model has appealing features for studying gene expression during the establishment, maintenance and reactivation phases of the HSV-2 quiescent state in cell culture. *Journal of Neuro Virology* (2000) 6, 296–302.

22 Claims, 3 Drawing Sheets

OTHER PUBLICATIONS

Martin JR, Suzuki S (1989). Targets of infection in a herpes simplex–reactivation model. *Acta Neuropathol (Berl)* 77: 402–411.

Miller CS, Smith KO (1991). Enhanced replication of herpes simplex virus type 1 in human cells. *J Dent Res* 70: 111–117.

Mitchell WJ, Deshmane SL, Dolan A, McGeoch DJ, Fraser NW (1990). Characterization of herpes simplex virus type 2 transcription during latent infection of mouse trigeminal ganglia. *J Virol* 64: 5342–5348.

Russell J. Preston CM (1986). An in vitro latency system for herpes simplex virus type 2. *Gen Virol* 67: 397–403.

Stephanopoulos DE, Kappes JC, Bernstein DI. (1988). Enhanced in vitro reactivation of herpes simplex virus type 2 from latently infected guinea–pig neural tissues by 5–azacytidine. *J Gen Virol* 69: 1079–1083.

Wang K, Pesnicak L, Straus SE (1997). Mutations in the 5' end of the herpes simplex virus type 2 latency–associated transcript (LAT) promoter affect LAT expression in vivo but not the rate of spontaneous reactivation of genital herpes. *J Virol* 71: 7903–7910.

Wigdahl BL, Isom HC, Rapp F (1981). Repression and activation of the genome of herpes simplex viruses in human cells. *Proc Natl Acad Sci* 78: 6522–6526.

Wilcox CL, Smith RL, Freed CR, Johnson Jr EM (1990). Nerve growth factor–dependence of herpes simplex virus latency in peripheral sympathetic and sensory neurons in vitro. *J Neuroscience* 10: 1268–1275.

Yoshikawa T, Stanberry LR, Bourne N, Krause PR (1996). Downstream regulatory elements increase acute and latent herpes simplex virus type 2 latency–associate transcript expression but do not influence recurrence phenotype or establishment of latency. *J Virol* 70 1535–1541.

Yura Y, Terashima K. Iga H, Yanagawa T, Yoshida H, Hayashi Y, Sato M (1986). A latent infection of herpes simplex virus type 2 in a neuroblastoma cell line IMR–32. *Arch Virol* 90: 249–260.

Millhouse and Wigdahl (2000) Molecular circuitry regulating herpes simplex virus type 1 latency in neurons.

Danaher, R.J. et al., Herpesvirus quiesence in neuronal cells: Antiviral conditions not required to establish and maintain HSV–2 quiesence. *Journal of NeuroVirology* 6, 296–302 (2000).

Su, Y. et al., Human Corneal Cells and Other Fibroblasts Can Stimulate the Appearance of Herpes Simplex Virus from Quiescently Infected PC12 Cell. *Journal of Virology* 73(5):4171–4180, May 1999.

Hardwicke, M. et al., Differential Effects of Nerve Growth Factor and Dexamethasone on Herpes Simplex Virus Type 1 oriL– and oriS–Dependent DNA Replication in PC12 Cells. *Journal of Virology* 71(5):3580–3587, May 1997.

Block, T. et al., Long term herpes simplex virus type 1 infection of nerve growth factor–treated PC12 cells. *Journal of General Virology* 75:2481–2487 (1994).

Greene, L.A., Nerve Growth Factor Prevents the Death and Stimulates the Neuronal Differentiation of Clonal PC12 Pheochromocytoma Cells in Serum–Free Medium. *Journal Cell Biology*, 78:747–755.

Gunning, P.W. et al., Nerve Growth Factor–Induced Diferentiation of PC12 Cells: Evaluation of Changes in RNA and DNA Metabolism. *Journal of Neuroscience* 1:1085–1095 (1981).

Halford, W.P. et al., Mechanisms of Herpes Simplex Virus Type 1 Reactivation. *Journal of Virology* 70:5051–5060 (1996).

Hammer, S.M. et al., Activation and Suppression of Herpes Simplex Virus in a Human Type Lymphoid Cell Line. *Journal of Immunology* 127:144–148 (1981).

Harris, R.A. et al., Establishment of Latency in vitro by the herpes simplex virus type 1 mutant in 1814. *Journal of General Virology* 72:907–913 (1991).

O'Neill, F.J., Prolongation of Herpes Simplex Virus Latency in Cultured Human Cells by Temperature Elevation. *Journal of Virology* 24:41–45 (1977).

O'Neill, F.J. et al., Herpes Simplex Virus Latency in Cultured Human Cells Following Treatment with Cytosine Arabinoside. *Journal of General Virology* 14:189–197 (1972).

Russell, J. et al., Herpes Simplex Virus Genes Involved in Latency in vitro. *Journal of General Virology* 68:3009–3018 (1987).

Scheck, A.C. et al., Transcriptional Activity of the Herpes Simplex Virus Genome during Establishment, Maintenance, and Reactivation of in vitro Virus Latency. *Intervirology* 30:121–136 (1989).

Smith, R.L. et al., Regulation of the Herpes Simplex Latency–Associated Transcripts during Establishment of Latency in Sensory Neurons in Vitro. *Journal of Virology* 202:49–60 (1994).

Wigdahl, B.L. et al., Activation of Herpes Simplex Virus (HSV) Type 1 Genome by Temperature–Sensitive Mutants of HSV Type 2. *Journal of Virology* 116:468–479 (1982a).

Wigdahl, B.L. et al., Herpes Simplex Virus Latency and Reactivation in Isolated Rat Sensory Neurons. *Journal of Virology* 127:159–167 (1983).

Wigdahl, B.L. et al., High Efficiency Latency and Activation of Herpes Simplex Virus in Human Cells. *Journal of Science* 217:1145–1146 (1982b).

Wilcox, C.L., et al., Nerve Growth Factor Deprivation Results in the Reactivation of Latent Herpes Simplex Virus In Vitro. *Journal of Virology* 61:2311–2315 (1987).

Wilcox, C.L. et al., Characterization of Nerve Growth Factor–Dependent Herpes Simplex Virus Latency in Neurons In Vitro. *Journal of Virology* 62:393–399 (1988).

\* cited by examiner

NEURONAL CELL MODEL AND METHODS OF USE THEREOF

CROSS REFERENCE TO RELATED APPLICATION

The present application claims the benefit of priority to U.S. Provisional Application No. 60/243,701, filed Oct. 27, 2000. The contents of this provisional application are incorporated herein by reference in its entirety.

FIELD OF THE INVENTION

The present invention relates, in general, to neurally-differentiated cells infected with viruses in a manner that supports a long-term non-productive infection for experimentation concerning the reactivation, induction, suppressing of virus latency.

BACKGROUND OF THE INVENTION

Herpes simplex virus types 1 and 2 (HSV-1 and -2) are alphaherpesviruses with similar, but unique molecular (Kieff et. al., 1971, 1972), biological and clinical features (reviewed in Whitley, 1996). The genomes are approximately 150 kb in size and each contains corresponding sets of 74 genes (Dolan et al, 1998). Both viruses infect epithelium, with HSV-1 having a predilection for orofacial sites and HSV-2 preferentially infecting genital surfaces. During the primary infection, HSV invades local nerve endings and travels to sensory ganglia where it can colonize neuronal nuclei and establish a latent state (*Hill* et al, 1972, Stevens and Cook, 1971). Reactivation of HSV from latency occurs intermittently as a result of stressful stimuli (e.g., trauma and heat). Reactivated viruses are responsible for causing recurrent epithelial infections that can occur in up to 89% of infected individuals (Benedetti, et. al. 1994).

The lack of a universally accepted neural cell culture model that supports HSV latency, in particular, HSV-2, restricts our understanding of the molecular events involved in reactivation from latency. Although animal models reproduce certain aspects of HSV-2 latency in humans (Al-Saadi et al, 1988; Bourne et al, 1994; Croen et al, 1991; Krause et al, 1995; Kurata et al, 1978; MacLean et al, 1991; Martin and Suzuki, 1989; Mitchell et al, 1990; Stanberry et al, 1982; Stephanopoulos et al, 1988; Wang et al, 1997; Yoshikawa et al, 1996), limitations in these models make interpretation of reactivation data challenging. Animal models limitations include: (i) latency and reactivation events that are influenced by viral strains with different primary growth phenotypes, (ii) the limited number of neurons latently infected in animal models (Bloom et al, 1996; Hill et al, 1996; Maggioncalda et al, 1996; Mehta et al, 1995; Ramakrishnan 1994; Sawtell, 1997; Sawtell et al, 1998; Thompson and Sawtell, 1997), and (iii) inaccurate quantitation of reactivation events when measuring virus production at the recurrent site as a result of influences of transport, replication in epithelium, and the immune response.

In response to these limitations, tissue and cell culture models of HSV-2 latency have been developed in an attempt to overcome limitations of animal models. A major advantage of tissue and cell culture models includes the ability to observe virus at the single cell level without the overlay of immunological events that modulate the eventual appearance of virus in the host. In addition, tissue culture models derived from neuronal and sympathetic ganglia have properties of the in vivo system including: (i) restricted transcription of the HSV genome (Doerig et al, 1991; Halford et al, 1996; Smith et al, 1992; Smith et al, 1994), (ii) lack of virus production following removal of the inhibitory agent, (Wilcox and Johnson, 1988) (iii) the presence of latency-associated transcripts (LATs) (Doerig et al, 1991; Smith et al, 1994), (iv) impaired reactivation of thymidine kinase negative virus (Wilcox et al, 1992), and (v) inducible reactivation (Halford et al, 1996; Moriya et al, 1994; Smith et al, 1992; Wilcox and Johnson, 1988; Wilcox and Johnson 1987; Wilcox et al, 1990). Nevertheless, tissue culture models have their drawbacks, preparation of dissected ganglia is inconvenient, material is limited, animal use is required, and axotomy introduces traumatic factors that influence reactivation of virus.

Accordingly, development of cell culture models with neuronal characteristics that lack the restrictive requirements of tissue culture models would be advantageous for understanding the molecular mechanisms of the establishment, maintenance and reactivation stages of HSV latency. Cell culture models also allow for an unlimited supply of a defined host cell and the ability to manipulate genetic material.

Over the past 25 years, cell culture systems using fibroblast cultures (Harris and Preston, 1991; Jamieson et al, 1995; O'Neill, 1977; O'Neill et al, 1972; Russell et al, 1987; Scheck et al, 1989; Wigdahl et al, 1982a; Wigdahl et al, 1982b; Wigdahl et al, 1983) and lymphocytes (Hammer et al, 1981; Youssoufian et al, 1982) have enabled the study of HSV-1 during a latent-like state. These models, however required low input multiplicities and/or the use of replication inhibitors such as anti-viral agents, inhibitory temperatures, or the use of a mutant virus, to prevent virus production. A cell line that has neural morphology and physiology, can survive infection and permit viral production, allow establishment of a long term nonproductive viral infection, and support virus in a state suitable for reactivation studies would be more desirable.

More recently, it has been reported that neurally-differentiated PC12 (ND-PC12) cells can harbor HSV-1 in a quiescent, yet reversible state (Danaher et. al., 1999a). These quiescently infected ND-PC12 cultures (QIF-PC12) demonstrate forskolin- and heat stress (HS)-inducible virus production in a high percentage (50–100%) of cultures for up to 8 weeks after infection, whereas mock-induced cultures maintain the quiescent viral state in the majority of infected cultures (Danaher et al, 1999b). In contrast to these cell culture models, the present invention, however, does not require antiviral conditions to maintain and/or establish the latent-like state (Colberg-Poley et al, 1979, 1981; Harris et al, 1989; Kondo et al, 1990; O'Neill, 1977; O'Neill et al, 1972; Russell et al, 1987; Russell and Preston, 1986; Wigdahl et al, 1981; Wilcox and Johnson, 1988; Wilcox et al, 1990; Yura et al, 1986).

The present application demonstrates that ND-PC12 cells permit establishment of an HSV-2 quiescent state, like HSV-1, following transient acycloguanosine (ACV) treatment. Unlike HSV-1, however, antiviral conditions are not required for the establishment of the HSV-2 quiescent state. In addition, the present invention discloses quiescent cultures in the presence of Vero cells, and the presence of Vero cells enhances the sensitivity to detect HSV-2 produced spontaneously and following induction (i.e., forskolin and HS treatment). Thus, the present invention demonstrates that ND-PC 12 cells can harbor HSV-2, like HSV-1, in a cryptic and non-productive state that is reversible, and this model has appealing features for studying gene induction during the establishment and maintenance of virus latency and the activation of HSV-2 from a nonproductive state.

SUMMARY OF THE INVENTION

A primary object of the present application is to provide neurally-differentiated cells infected with viruses in a manner that supports a long-term non-productive infection for experimentation. Another object of the present invention also provides a cell culture research model for HSV-2 quiescent infection in ND-PC12 cells to investigate quiescent and reactivation properties of HSV-2. This model represents an improvement over existing cell culture models for HSV-1. Advantages of this quiescently infected PC12 cell culture model include: (1) establishment and maintenance of a HSV-2 quiescent infection in a high proportion of PC12 cell cultures with and without the transient use of ACV (acyclovir); (2) the ability to produce HSV-2 from a quiescent state in response to forskolin and HS treatment for at lest 4 weeks post infection; and (3) the ability to discriminate between quiescence, spontaneous reactivation and inducible reactivation using a range of multiplicities of infection (MOIs). Thereby, these enhanced features of the invention enable analysis of the establishment and maintenance of latency and the reactivation events of a cryptic HSV genome at the single neural cell level in vitro.

Accordingly, additional objects of the present invention provide for methods of establishing quiescently-infected PC12 cells, reactivating quiescent virus, determining the ability of a test reagent to suppress and/or induce virus reactivation, eliciting phenotypic change in a PC12 cell, determining the susceptibility to reactivation of a person infected with a quiescent virus, identifying nucleic acid molecules and/or proteins involved in virus reactivation, identifying the origins of DNA replication important to virus reactivation, screening an altered virus' ability to be reactivated, determining the ability of a non-neurotropic virus to become quiescent and/or reactivatable, and a method of determining a reagent's ability to inhibit establishment of quiescent viral infection.

Additional objects and attendant advantages of the present invention will be set forth, in part, in the description that follows, or may be learned from practicing or using the present invention. The objects and advantages may be realized and attained by means of the instrumentalities and combinations particularly recited in the appended claims. It is to be understood that the foregoing general description and the following detailed description are exemplary and explanatory only and are not to be viewed as being restrictive of the invention, as claimed.

The present invention provides, inter alia, neural cells comprising a PC12 cell quiescently infected with a neurotropic virus. Preferred quiescently-infected neural cells are those wherein the neurotropic virus is a neurotropic herpes virus. More preferred are quiescently-infected neural cells wherein the neurotropic virus is a neurotropic human herpes virus. More preferred are quiescently-infected neural cells wherein the neurotropic herpes virus is a human herpes simplex 2 virus. However, those quiescently-infected neural cells wherein the neurotropic virus is selected from the group consisting essentially of varicella zoster viruses, polyoma viruses, measles viruses, human immunodeficiency viruses, papillomaviruses, adenoviruses, cytomegaloviruses, epstein barr viruses, hepatitis viruses, coronaviruses, coxsackie viruses, rabies viruses, flaviviruses, paramyxoviruses, togaviruses, and rhinoviruses, are also preferred.

Also provided are methods of establishing quiescently-infected neural cells, comprising introducing a neurotropic virus to neurally-differentiated and viable PC12 cells in a serum-free medium, said differentiated PC12 cells being in a container; and incubating said container with an antiviral reagent for a time necessary to accomplish quiescence of viral activity; and removing said antiviral agent from said container. Preferred such methods are those wherein the neurotropic virus is a neurotropic herpes virus. More preferred are those methods wherein the neurotropic herpes virus is a human herpes simplex 2 virus. However, those methods wherein the neurotropic virus is selected from the group consisting essentially of varicella zoster viruses, polyoma viruses, measles viruses, human immunodeficiency viruses, papillomaviruses, adenoviruses, cytomegaloviruses, epstein barr viruses, hepatitis viruses, coronaviruses, coxsackie viruses, rabies viruses, flaviviruses, paramyxoviruses, togaviruses, and rhinoviruses are also preferred. Methods wherein the neurotropic herpes virus is a human herpes simplex 2 virus and the antiviral agent is acyclovir are preferred, especially those methods wherein said container is incubated with an antiviral composition for approximately five (5) to twelve (12) days, more especially methods wherein said container is incubated at a temperature less than 40 degrees Celsius (40° C.), and most especially wherein said serum free medium allows for constant cell density and imparts neural characteristics to said cells.

Importantly, also provided are methods of establishing quiescently-infected neural cells without using an antiviral reagent, comprising introducing a neurotropic virus to neurally-differentiated and viable PC12 cells in a serum-free medium; replenishing the serum-free medium after introduction of the neurotropic virus to maintain acceptable cell viability. Preferably, the medium is replenished daily for three (3) days, and thereafter, every two (2) to three (3) days until experimentation.

Also provided are methods of reactivating a quiescent virus from neural cell, comprising: introducing a reactivator to any of the herein described quiescently-infected neural cells.

Also provided are methods for determining the ability of a test reagent to suppress virus reactivation from a quiescently-infected neural cell, comprising introducing a test reagent to a quiescently-infected neural cell described herein; and introducing to said neural cell a reactivator; and determining if reactivation has been suppressed.

Also provided are methods for determining the ability of a test reagent to induce virus reactivation in a neural cell, comprising introducing a test reagent to a quiescently-infected neural cell described herein; and determining if reactivation has been induced.

Also provided are methods for determining the ability of a test reagent to establish virus latency in a neural cell, comprising introducing a test reagent to a quiescently-infected neural cell described herein; and determining if latency has been induced.

Also provided are methods for determining the ability of a test reagent to inhibit establishment of a quiescent viral infection, comprising introducing a virus to differentiated and viable PC12 cells; replenishing the serum-free medium after introduction of the non-neurotropic virus to maintain acceptable cell viability. Preferably, the medium is replenished daily for three (3) days, and thereafter, every two (2) to three (3) days until experimentation.

Also provided are methods for eliciting phenotypic change in a neural cell, introducing a reactivator to a quiescently-infected neural cell described herein, and eliciting a phenotypic change in said neural cell. Preferred are such methods wherein said phenotypic change is selected from the group consisting of synthesis of myelin, synthesis of neurotransmitter, cell death, and viral shedding.

Also provided are methods for determining the susceptibility of a person infected with a quiescent virus to reactivation by a reagent, comprising introducing a reactivator to a quiescently-infected neural cell described herein, wherein the neurotropic virus is a strain isolated from a person infected with said neurotropic virus; and determining the relative magnitude of phenotypic or genomic reactivation.

Also provided are methods to identify nucleic acid molecules and/or proteins involved in virus reactivation, comprising reactivating a quiescently-infected neural cell described herein with a reactivator; and identifying nucleic acid molecules and/or proteins which are uniquely expressed during reactivation.

Also provided are methods to identify the origins of DNA replication important to virus reactivation, comprising reactivating a quiescently-infected neural cell described herein with a reactivator; and identifying the origins of replication which are uniquely associated with reactivation.

Also provided are methods to identify nucleic acid molecules and/or proteins involved in establishing and maintaining virus latency, comprising establishing latency of a neural cell described herein according to the methods described herein; and identifying nucleic acid molecules and/or proteins which are uniquely expressed during latency.

Also provided are methods to identify the origins of DNA replication important to establishing and maintaining virus latency, comprising establishing latency of a neural cell described herein according to the methods described herein; and identifying nucleic acid molecules and/or proteins which are uniquely expressed during latency.

Also provided are methods to screen an attenuated virus' relative ability to be reactivated, comprising introducing a reactivator to a quiescently-infected neural cell described herein, wherein the neurotropic virus is an attenuated virus; and determining the relative magnitude of reactivation.

Also provided are methods to determine the ability of a virus to become quiescent and/or reactivatable in a neural cell line, comprising introducing a non-neurotropic virus to differentiated and viable PC12 cells in a serum-free medium; replenishing the serum-free medium after introduction of the neurotropic virus to maintain acceptable cell viability. Preferably, the medium is replenished daily for three (3) days, and thereafter, every two (2) to three (3) days until experimentation.

DEFINITIONS

For the purposes of the present application, the following terms shall have the following meanings:

"a" or "an", when describing a noun, refers to one or more of that noun.

"acceptable cell viability" means sufficient viability of quiescently infected cells to perform experiments.

"antiviral reagent" means a reagent which prevents viral growth or DNA replication in a cell.

"composition" means any compound or composition made by any means. "Composition" includes synthetic or naturally-occurring compounds or compositions, whether purified or not, and can include: biologicals, chemicals, herbal extract(s); precursor(s); metabolite (s); and ingredient(s), including enantiomer(s) of a racemic mixture. The definition of "composition" includes compounds produced in situ by virtue of an immune response (i.e., immunoglobulins and compounds involved in inflammation), as well as organisms, such as: viruses, bacteria and fungi.

"isolated" means physically removed from a form found in nature. For instance, whole cells, a crude cell extract, purified virus, molecularly engineered virus, or artificial virus would be "isolated" virus.

"neurotropic virus" means any virus which is capable of infecting neurons, including viruses which only transiently infect neurons.

"quiescent" or "quiescence" means the absence of detectable infectious particles in the media and within the cells having viral nucleic acid present in the cells.

"reactivator" means a reagent which will cause reactivation of quiescent virus.

"reactivation" means any change in phenotype or genotype from a quiescent state.

"reagent" means a composition or an environmental condition, temperature, ultraviolet radiation, biological, etc.

"virus" means the definition as understood by those in the art, as well as viroid particles such as prions, and including natural and artificial alterations thereof (eg. mutations (eg. temperature sensitive mutations), including deletions, insertions, etc.)

DESCRIPTION OF THE INVENTION

Figure 1:
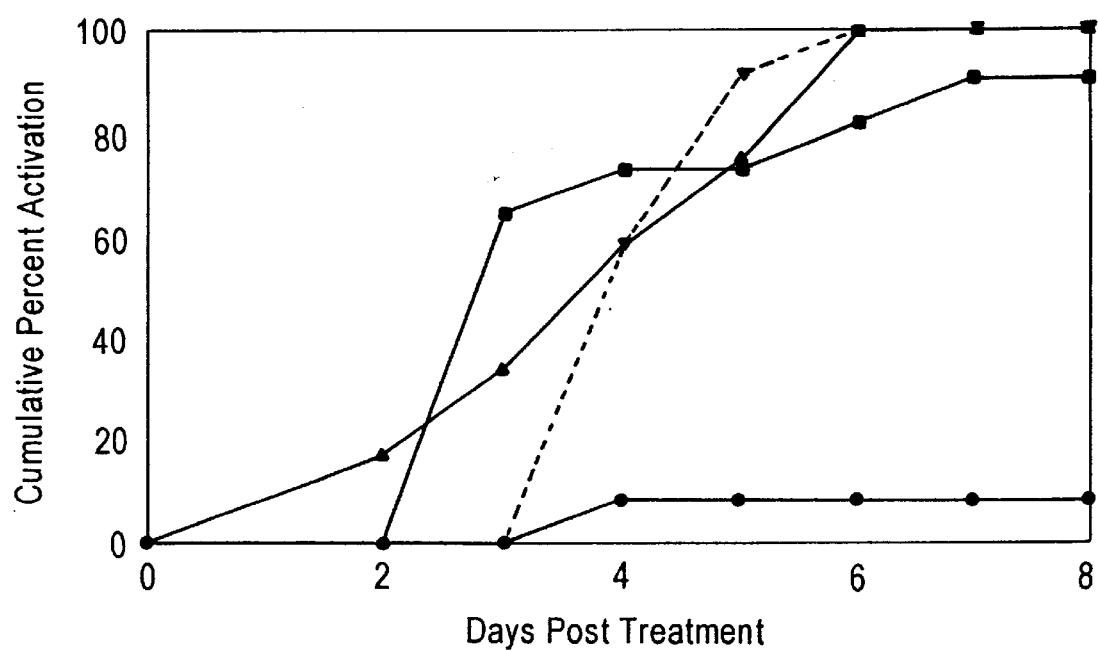
FIG. 1 shows induction of HSV-2 from QIF-PC12 cell cultures. Nonproductive cultures subjected to 50 $\mu$M forskolin (▲), HS (43° C., 3 h) (■), or mock-induction (●) on day 15 p.i. Parallel cultures cocultivated with Vero cells 2 days after the forskolin induction (————▼————).

All patents, patent applications and literatures cited in this description are incorporated herein by reference in their entirety. In the case of inconsistencies, the present disclosure, including definitions, will prevail.

The mechanisms that govern HSV-2 reactivation from latency remain unknown. An obstacle to understanding HSV-2 latency and reactivation has been the lack of in vitro models that permit analysis of HSV-2 quiescence and induction at the neuronal and clonal cell level. In a preferred embodiment, the present invention is neurally-differentiated cells infected with viruses in a manner that supports a long-term nonproductive infection for experimentation. Also in a preferred embodiment, the invention is directed to a cell culture research model for HSV-2 quiescent infection in ND-PC12 cells to investigate quiescent and reactivation properties of HSV-2. This model represents an improvement of existing cell culture models for HSV-1. Advantages of the QIF-PC12 cell culture model include: (1) establishment and maintenance of a HSV-2 quiescent infection in a high proportion of PC12 cell cultures with and without the transient use of ACV; (2) the ability to produce HSV-2 from a quiescent state in response to forskolin and HS treatment for as long as 4 weeks post infection; and (3) the ability to discriminate between quiescence, spontaneous reactivation and inducible reactivation using a range of MOIs. Thereby these enhanced features of the invention enable the analysis of reactivation events of a cryptic HSV genome at the single neural cell level in vitro.

The present invention provides, inter alia, neural cells comprising a PC12 cell quiescently infected with a neurotropic virus. Preferred quiescently-infected neural cells are those wherein the neurotropic virus is a neurotropic herpes virus. More preferred are quiescently-infected neural cells wherein the neurotropic virus is a neurotropic human herpes virus. More preferred are quiescently-infected neural cells wherein the neurotropic herpes virus is a human herpes simplex 2 virus. However, those quiescently-infected neural cells wherein the neurotropic virus is selected from the group consisting essentially of varicella zoster viruses, polyoma viruses, measles viruses, human immunodeficiency viruses, papillomaviruses, adenoviruses, cytomegaloviruses, epstein barr viruses, hepatitis viruses, coronaviruses, coxsackie viruses, rabies viruses, flaviviruses, paramyxoviruses, togaviruses, and rhinoviruses, are also preferred.

Certain PC12 cells are available commercially as described in the examples. PC12 cell variants are within the scope of the present invention, as are any cells derived from the neural crest. These materials can be commercially obtained from American Type Culture Collection (ATCC, Rockville, Md.) or other commercial entities. These cells are within the scope of the present invention as well. There are eight (8) types of herpes virus. For instance, human herpes virus 1, human herpes virus 2, human herpes virus 6, human herpes virus 7, and human herpes viruses 8 are "types" of human herpes virus. Within the meaning of each of the viruses listed in the claims are several hundreds of "strains" of those viruses. The strains of each virus type are, of course, included within the scope of the present invention. For instance, human HSV-2 includes the strains listed in the examples, as well as these other strains, such as G and 333 HSV-2 strains.

Viruses can be obtained by purchasing them commercially (as part of a cell line or tissue sample) from ATCC or by obtaining them according to the procedures well known in the art, such as by obtaining clinical isolates, or cultures from researchers in the field. Textbooks which discuss manipulations of viruses are many, including: Fields & Knipe, Fundamental Virology; Luria et al, General Virology; and Fenner et al., Molecular Virology. The present quiescently-infected neural cells can be made by the methods disclosed herein.

Particularly useful in the preparation of the neural cells are the examples, although variations as described herein will also produce the present materials. Moreover, certain reasonable optimization of the methods can be accomplished according to methods well-known in the art.

In addition, a significant aspect of this invention provides the methods of establishing quiescently-infected neural cells. One such method comprises introducing a neurotropic virus to neurally-differentiated and viable PC12 cells in a serum-free medium, said differentiated PC12 cells being in a container; and incubating said container with an antiviral reagent for a time necessary to accomplish quiescence of viral activity; and removing said antiviral agent from said container. Preferred methods comprise human herpes simplex 2 virus as the neurotropic herpes virus and acyclovir as the antiviral agent, especially wherein said container is incubated with an antiviral composition for approximately five (5) to twelve (12) days, more especially wherein said container is incubated at a temperature less than 40 degrees Celsius (40° C.), and most especially wherein said serum free medium allows for constant cell density and imparts neural characteristics to said cells. However, those methods which also include a neurotropic virus selected from the group consisting essentially of varicella zoster viruses, polyoma viruses, measles viruses, human immunodeficiency viruses, papillomaviruses, adenoviruses, cytomegaloviruses, epstein barr viruses, hepatitis viruses, coronaviruses, coxsackie viruses, rabies viruses, flaviviruses, paramyxoviruses, togaviruses, and rhinoviruses are also preferred.

Another such method of establishing quiescently-infected neural cells comprises introducing neurotropic virus to neurally-differentiated and viable PC12 cells in a serum-free medium, and replacing the serum-free culture medium with fresh serum-free media to maintain acceptable neurally-differentiated cell's viability. Preferably the culture media is replenished daily for three (3) days after introduction of the neurotropic virus to the neurally-differentiated PC12 cells, and thereafter, every two (2) to three (3) days until experimentation. Further preferred methods are those wherein the neurotropic virus is a neurotropic herpes virus and still more preferred are those methods wherein the neurotropic herpes virus is a human herpes simplex 2 virus. However, those methods which also include a neurotropic virus selected from the group consisting essentially of varicella zoster viruses, polyoma viruses, measles viruses, human immunodeficiency viruses, papillomaviruses, adenoviruses, cytomegaloviruses, epstein barr viruses, hepatitis viruses, coronaviruses, coxsackie viruses, rabies viruses, flaviviruses, paramyxoviruses, togaviruses, and rhinoviruses are also preferred.

The methods described herein may utilize the specific conditions described in the examples, but may also vary therefrom. Variations include the use of collagen in the plating technique; collagen need not be used, but efficiency will be improved if it is. Moreover, the plates need not be as confining as described in the examples; other surfaces, including different shapes and sizes, can be used, so long as a viable cell culture can be maintained for the length of time desired. The multiplicity of infection may be from 0.5 to greater than 15, although the examples describe preferred higher multiplicities for HSV-2 when high reactivation rates are desired. However, in certain instances, it may be optimal to have low reactivation rates, depending on the particular use of the neural cells. In that case, lower multiplicities would be optimal. The antiviral reagent used can be any which causes quiescence of the neurotropic virus. The exemplified reagent, acycloguanosine, may be optimized chemically for this purpose, or other antivirals may be used. For example, zidovudine (AZT), lamivudine (3TC) indinavir (IDV), ganciclovir, famiciclovir, foscarnet, idoxyuridine, phosphoacetic acid, 5-fluorouracil, or similar compounds and analogs thereof may be used. The concentrations of the compound used to cause quiescence can also be modified as necessary. Moreover, a combination (eg. two or more) of antiviral drugs may be used. Incubation of the PC12 cells with the antiviral is optimally that described in the examples, but can be more or less, depending on the particular reagent used. Optimization of the incubation schedule is within the skill of the art. Lastly, the media used can be any that allows viable cell growth, so long as it allows for constant cell density and may be supplemented reagent or virus in order to transiently inhibit viral growth. It is optimal to change the media as described in the examples, but it is not necessary, so long as the cells are acceptably viable.

Also provided are methods of reactivating a quiescent virus from neural cell, comprising: introducing a reactivator to a quiescently-infected neural cell described herein. This aspect of the invention is particularly useful in studying reactivation, as well as in studying quiescence. The information gleaned from reactivation and quiescence studies will be of benefit in drug discovery. The preferred quiescently-infected neural cells for use in this embodiment are those comprising neurotropic herpes viruses, preferably HSV-2. The neural cells can be prepared as described herein and introducing a reactivator can be accomplished according by any means which causes reactivation.

Also provided are methods for determining the ability of a test reagent to suppress virus reactivation from a quiescently-infected neural cell, comprising, introducing a test reagent to a quiescently-infected neural cell described herein; and introducing to said neural cell a reactivator; and determining if reactivation has been suppressed. This aspect of the invention is particularly useful for identifying potential anti-viral drugs. The preferred quiescently-infected neural cells for use in this embodiment are those comprising neurotropic herpes viruses, preferably HSV-2. The neural cells can be prepared as described herein; introducing a reactivator can be accomplished by any means which causes reactivation; and determining reactivation can be accomplished by any means, including, for example, those means described in the examples, or other well-known means.

Also provided are methods for determining the ability of a test reagent to induce virus reactivation from a neural cell, comprising introducing a test reagent to a quiescently-infected neural cell described herein; and determining if reactivation has been induced. This aspect of the invention is particularly useful for identifying potential reactivators. In one aspect, this embodiment is useful in drug discovery as part of a toxicology screen. For example, if a reagent such as a drug (or potential drug), vaccine, carrier, food, or environmental condition is implicated through the use of this method as a reactivator of quiescent virus, it would be advisable for an infected individual to avoid the reagent, since reactivation of virus is normally detrimental to the individual. The preferred quiescently-infected neural cells for use in this embodiment are those comprising neurotropic herpes viruses, preferably HSV-2. The neural cells can be prepared as described herein; introducing a test compound can be accomplished by any means which causes interaction between the test compound and the neural cells; and determining reactivation can be accomplished by any means, including, for example, those means described in the examples, or other well-known means.

Also provided are methods to determine a reagent's ability to inhibit establishment of a viral infection, comprising introducing a virus to differentiated and viable PC12 cells in a serum-free, test reagent-containing medium, said differentiated PC12 cells being in a container; and incubating said container with an antiviral reagent for a time necessary to accomplish quiescence of viral activity in the absence of said test reagent; and removing said antiviral agent from said container; and determining said test reagent's ability to inhibit quiescence. This aspect of the invention is particularly useful for identifying reagents which could be used as an anti-viral drug. The reagents identified as inhibiting the establishment of quiescence would be particularly effective to administer during the first lytic phase of a viral infection. Additionally, methods to determine a reagent's ability to inhibit establishment of a viral infection, comprise introducing a virus to differentiated and viable PC12 cells in a serum-free, test reagent-containing medium, replacing the serum-free medium with fresh serum-free, test reagent-containing medium after introduction of the non-neurotropic virus to the differentiated PC12 cells to maintain acceptable differentiated PC12 cell viability. Preferably, the media is replenished daily for three (3), and thereafter, every two (2) to three (3) days. The preferred neural cells for use in this embodiment are those which are neurotropic herpes viruses, specifically HSV-2.

Also provided are methods for eliciting phenotypic change in a neural cell, introducing a reactivator to a quiescently-infected neural cell described herein, and eliciting a phenotypic change in said neural cell. Preferred are such methods wherein said phenotypic change is selected from the group consisting of synthesis of myelin, synthesis of neurotransmitter, degradation of neurotransmitters, cell death, and viral shedding. This aspect of the invention is particularly useful in studying disease states, such as multiple sclerosis, or other neuron-associated diseases. The neural cells can be directed via molecular techniques, for example, to result in disease state upon activation. Alternatively, the neural cells can be directed to be positive influences on the environment, such that gene therapy studies will be possible using this embodiment. In all aspects of the present embodiment, the methods will be useful for drug discovery in that the mechanisms of phenotypic change can be studied. The preferred quiescently-infected neural cells for use in this embodiment are those comprising neurotropic herpes viruses, preferably HSV-2.

Also provided are methods for determining the susceptibility of a person infected with a quiescent virus to reactivation by a reagent, comprising introducing a reactivator to a quiescently-infected neural cell described herein, wherein the neurotropic virus is a strain isolated from a person infected with said neurotropic virus; and determining the relative magnitude of phenotypic or genomic reactivation. This aspect of the present invention is particularly useful for patient diagnosis and directed medical care. Since some strains are more reactivatable than others are, it is important to determine the aggressiveness and/or timing of treatment. The present embodiment, for example, can identify those individuals who harbor a strain particularly reactivatable by sunlight, in which those patients could use sunscreen or avoid the sun. The method would provide information to patients who have a less reactivatable strain, so that suppressor drug levels can be lowered in comparison to those who have a highly reactivatable strain. The preferred quiescently-infected neural cells for use in this embodiment are those comprising neurotropic herpes viruses, preferably HSV-2.

Also provided are methods to determine the ability of a non-neurotropic virus to become quiescent and/or reactivatable in a neural cell line, comprising introducing a non-neurotropic virus to differentiated and viable PC12 cells in a serum-free medium, said differentiated PC12 cells being in a container; and incubating said container with an antiviral reagent for a time necessary to accomplish quiescence of viral activity; and removing said antiviral agent from said container; and determining said non-neurotropic virus's ability to become quiescent and or reactivatable. In addition, methods are provided to determine the ability of a non-neurotropic virus to become quiescent and/or reactivatable in a neural cell line, comprising introducing a non-neurotropic virus to differentiated and viable PC12 cells in a serum-free medium, said serum-free medium being replenished with fresh serum-free media to maintain acceptable differentiated PC12 cell viability. Preferably the media is changed daily for the first three (3) days after introduction of the non-neurotropic virus, and thereafter every two (2) to three (3) days. This aspect of the present invention is particularly useful to identify additional viruses which may be amenable to the present invention. The preferred quiescently-infected neural cells for use in this embodiment are those comprising neurotropic herpes viruses, preferably HSV-2.

Also provided are methods to identify nucleic acid molecules and/or proteins involved in virus reactivation, comprising reactivating a quiescently-infected neural cell described herein with a reactivator; and identifying nucleic acid molecules and/or proteins which are uniquely expressed during reactivation. This aspect of the present invention is particularly useful for general scientific research or to study possible targets for drug discovery. The preferred quiescently-infected neural cells for use in this embodiment are those comprising neurotropic herpes viruses, preferably HSV-2.

Also provided are methods to identify the origins of DNA replication important to virus reactivation, comprising reactivating a quiescently-infected neural cell described herein with a reactivator; and identifying the origins of replication which are uniquely associated with reactivation. This aspect of the present invention is particularly useful for general scientific research or to study possible targets for drug discovery. The preferred quiescently-infected neural cells for use in this embodiment are those comprising neurotropic herpes viruses, preferably HSV-2.

Also provided are methods to screen an attenuated virus' relative ability to be reactivated, comprising introducing a reactivator to a quiescently-infected neural cell described herein, wherein the neurotropic virus is an attenuated virus; and determining the relative magnitude of reactivation. This aspect of the invention is particularly useful to determine the reactivatability of potential or actual vaccines. Vaccines which can reactivate, whether alone, or in combination with an additional reagent, would be potentially dangerous. In other words, this aspect of the invention can be used a specially-designed toxicology assay. The preferred quiescently-infected neural cells for use in this embodiment are those comprising neurotropic herpes viruses, preferably HSV-2.

EXAMPLE 1

Virus and Cells

Rat pheochromocytoma (PC12) and Vero (Africa green monkey kidney) cells were obtained from ATCC (Rockville, Md., USA). All culture media and supplements were purchased from Gibco BRL (Gaithersburg, Md., USA) unless otherwise indicated. PC12 cells were grown in RPMI 1640 media containing 5% fetal bovine serum (FBS) and 10% heat-inactivated horse serum. Vero cells were grown and maintained in M199 medium containing 5% FBS. Cells were incubated at 37° C. in humidified incubator with 5% $CO_2$. All media was supplemented with penicillin (100 units/ml) an (streptomycin (100 $\mu$g/ml). HSV-2 strain 333 was a kind gift from Philip R Krause (Food and Drug Administration, Bethesda, Md., USA). Viral stocks were prepared in Vero cells and maintained at −85° C.

In particular, the neuronally-differentiated PC12 cells were established from pheochromocytoma of rat adrenal medulla, and used to host a persistent viral infection. Neural differentiation of the PC12 cells comprises growing cells in defined medium containing nerve growth factor. Under these conditions cells extend neurites, develop electrical excitability and express genes encoding neuronal cell-specific proteins (Green and Tischler 1976; Green and Tischler 1982). Cells are maintained in serum-free medium to render them non-dividing. Next, cells are inoculated with neurotropic virus (eg., human herpes virus) under conditions that restrict viral propagation. A defined regimen of media changes is used to establish a quiescent and nonproductive state following the withdrawal of the antiviral treatment. Evidence of establishment of a quiescent and persistent infection comes from assays demonstrating that cells survive the infection, a nonproductive viral state is established in the majority of cultures, and cells support spontaneous and inducible virus production.

EXAMPLE 2

Morphologic Differentiation

For morphologic differentiation, PC12 cells were maintained in RPMI 1640 supplemented 0.1% bovine serum albumin, fraction V (BSA) and 50 ng/ml of 2.5S mouse nerve growth nerve factor (NGF) (Becton Dickinson) (maintenance media) throughout the studies, unless indicated, beginning on the day of plating. PC12 were plated, following two rinses with RPMI 1640 containing 0.1% BSA and dissociation by passage through a 22-gauge needle, in 12-well tissue culture dishes (Bector Dickinson Labware, Franklin Lakes, N.J., USA) coated with rat tail collagen type 1 (Bector Dickinson) at $1.1 \times 10^5$ cells/well in maintenance media. Collagen was applied as recommended by the supplier. Following 4 days of differentiation in maintenance media, cultures were maintained in RPMI 1640 supplemented with 10% horse serum (heat-inactivated) and 5% FBS, and 50 ng/ml NGF for 2 days. The following day cultures received maintenance media supplemented with 100 $\mu$M acycloguanosine (ACV) when indicated, purchased from Sigma (St. Louis, Mo., USA). Morphologic differentiation was confirmed by microscopic visualization of dendritic processes. Media was changed every 2 to 3 days unless indicated.

EXAMPLE 3

Establishment of a Quiescent Infection

ND-PC12 cells were infected in a volume of 0.4 ml/well in 12-well plates without agitation at the indicated multiplicity of infection (MOI) overnight at 37° C. When used, ACV was maintained in the medium from 1 day prior to infection 8 days post-infection (p.i.). After ACV withdrawal, a quiescent state (i.e., free of detectable infectious virus in culture supernatants) was maintained for at least 7 days prior to induction. At the indicated times, Vero cells were trypsinized, washed twice with RPMI and introduced into the QIF-PC12 cell cultures at a ratio of 1:1 in maintenance media.

EXAMPLE 4

Induction Stimuli and Assay of Virus Production

HSV QIF-PC12 cells, that were free of detectable infectious virus, were subjected to heat stress (43° C. for 3 h in an incubator), or maintenance media supplemented with or without 50 $\mu$M forskolin (Sigma) as previously described (Danaher et al, 1999a,b). Virus production was determined using 25% volume of supernatants from infected PC12 cultures in a direct plaque assay (DPA) on monolayers of Vero cells as previously described (Miller and Smith, 1991). Cultures were subsequently replenished with fresh maintenance media.

EXAMPLE 5

HSV-2 Establishes a Quiescent Infection in ND-PC12 Cells That is Reversible.

Preliminary data indicated that QIF-PC12 cell cultures established with HSV-2 produce virus following heat stress and forskolin and forskolin induction (data not shown). However, unlike previous findings with HSV-1, minimal amounts of virus (i.e., only a single plaque forming unit) were detected in the majority of QIF-PC12 cell cultures determined to be positive for HSV-2 production following induction. Furthermore, cocultivation of HSV-2 established QIF-PC12 cell cultures with Vero cells did not increase the proportion of cultures producing virus, but increased the amount of virus detected from such cultures. This indicated that HSV-2 was not induced from QIF-PC-12 cell cultures by cocultivation with Vero cells, and Vero cells could be used to increase the sensitivity of the system.

Based on these findings, forskolin and HS induced HSV-2 reactivation from QIF-PC12 cell cultures that were cocultivated with Vero cells was analyzed in more detail. QIF-PC12 cell cultures were established with strain 333 at MOI of 10 as described in the Materials and methods using transient ACV treatment. Cultures were cocultivated with Vero cells at a ratio of 1:1 three days before induction with forskolin or HS (day 15 p.i.). Virus production was monitored from day 10 through 23 p.i. Prior to induction, HSV-2 was detected infrequently (2.8%; 1/36) in cocultivated cultures. The 35 cultures that were not shedding virus were used in induction assays. Following induction treatment (FIG. 1), virus was detected in 90 to 100% of HS and forskolin induced cocultivated cultures, and 8.3% (1/12) of mock-induced cocultivated cultures. These data indicate that quiescently infected cultures can be established with HSV-2 and virus production can be induced by both physical and chemical stimuli.

The possibility that Vero cells influenced HSV induction from QIF-PC12 cell cultures was assessed in two ways. First, parallel neuronal cultures established with HSV-2 were cocultivated with Vero cells 2 days after induction with forskolin. This allowed for comparison of virus production occurring before and after cocultivation. Second, induction of HSV-1 established cultures was analyzed in the presence and absence of Vero cell cocultivation, as detection of HSV-1 progeny from such cultures does not require Vero cells (Danaher et al, 1999a). QIF-PC12 cell cultures were established with HSV-2 strain 333 at MOT of 10 with the transient use of ACV as described in the Material and methods. Cultures were cocultivated with Vero cells at a 1:1 ratio 3 days before induction. Nonproductive cultures were subjected to 50 μM forskolin, HS (43° C., 3 h), or mock-induction on day 15 p.i. Cultures were monitored for virus production using culture supernatants in the direct plaque assay. Virus was detected in 2.8%; (1/36) of cultures cocultivated before induction and 0% (0/12) of cultures cocultivated after induction between day of ACV withdrawal (day 8 p.i.) and day of induction. In HSV-2 established cultures (FIG. 1), virus was detected in a similar proportion of cultures by day 4 post-forskolin treatment whether cultures were cocultivated before or after induction.

Figure 2A:
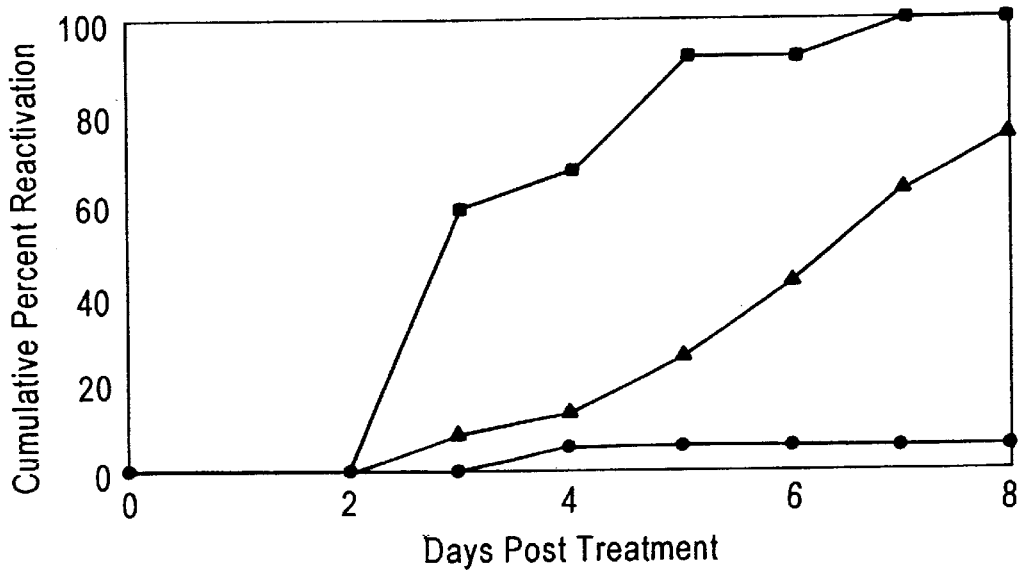
FIGS. 2A and 2B show the effect of cocultivation on induction of HSV-1 from QIF-PC12 cell cultures. Nonproductive QIF cultures subjected to 50 $\mu$M forskolin (▲), HS (43° C., 3 h) (■), or mock-induction (●) on day 15 p.i.
Figure 2B:
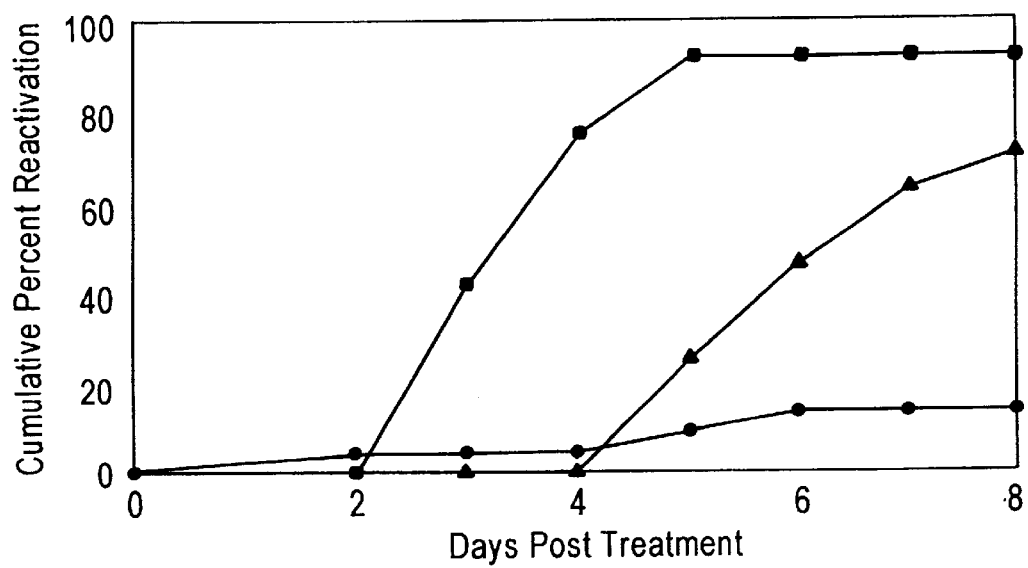

This indicated that the Vero cells did not contribute to induction of HSV-2, but merely allowed for detection of progeny virus. Results shown in FIG. 2 demonstrate that cocultivation of HSV-1 established QIF-PC12 cell cultures with Vero cells did not induce HSV-1 production or alter the efficiency of the response to forskolin and HS. QIF-PC 12 cell cultures were established with HSV-1 strain 17+ at MOI of 1 with the transient use of ACV as described in the Material and methods. Cultures were either mock cocultivated (A), or cocultivated with Vero cells at a 1:1 ratio 3 days before induction (B). Nonproductive QIF cultures were subjected to 50 μM forskolin, HS (43° C., 3 h), or mock-induction on day 15 p.i. Cultures were monitored for virus production using culture supernatants in the direct plaque assay. Virus was detected in 0% (0/72) mock cocultivated and 1.7% (1/60) Vero cocultivated cultures between the day of ACV withdrawal (day 8 p.i.) and day of induction.

Therefore, the findings from these two experiments demonstrate that cocultivation with Vero cells did not contribute to the reactivation response. Furthermore, HSV-1 and -2 established QIF-PC12 cell cultures can maintain a nonproductive state in the presence of Vero cells. This indicates that low amounts of infectious virus are not being chronically shed and the cultures are truly quiescent.

EXAMPLE 6

Long-Term HSV-2 Quiescent Infection in PC12 Cells Cocultivated With Vero Cells The ability of HSV-2 to maintain a short-term quiescent infection in ND-PC12 cells suggested such a state could be maintained long-term in the presence of Vero cell cocultivation. To assess this, QIF-PC12 cell cultures were established with HSV-2 as described above. Cultures were cocultivated with Vero cells at a ratio of 1:1 within 10 days of AC withdrawal. Induction was performed with forskolin on day 30 p.i. Cultures were monitored for virus production using culture supernatants. Over the 3 week period between ACV withdrawal and induction, 71% (17/24) of the HSV-2 infected culture maintained quiescence. HSV-2 was produced from 100% (8/8) of forskolin induced cultures and 0% (0/9) of mock induced cultures by 8 days post-induction (data not shown). These data indicate that long-term HSV quiescence can be maintained in QIF-PC12 cell cultures in the presence of Vero cell cocultivation and absence of ACV, and these cultures reactivate virus when induced with forskolin 30 days p.i.

EXAMPLE 7

Reactivation of HSV-2 is MOI Dependent

Figure 3:
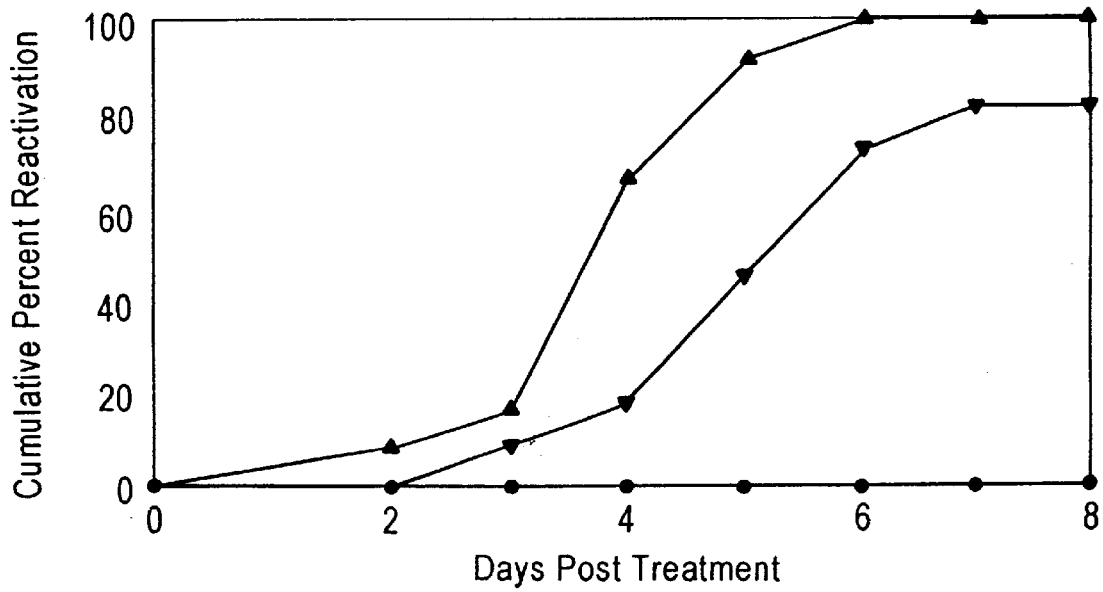
FIG. 3 shows that the reactivation of HSV-2 is multiplicity of infection (MOI) dependent. Nonproductive cultures subjected to 50 $\mu$M forskolin (▼, MOI=3), (▲, MOI=30), or mock-induction (●) on day 15 p.i.

Next, it was determined whether the efficiency of HSV-2 activation from quiescence was MOI-dependent. QIF-PC12 cell cultures were established with HSV-2 strain 333 at MOIs of 3 and 30 and cocultivated with Vero cells at a ratio of 1:1 on day 12 p.i. as above. Nonproductive cultures harboring a quiescent infection on day 15 p.i. were subjected to forskolin (50 μM) or mock induction. Virus production was monitored using cultured supernatants as described above. Between the period of ACV withdrawal and induction, virus was detected in 4.2% (1/24) of cultures for each MOI. FIG. 3 shows that viral MOI influenced the efficiency of HSV-2 activation from quiescence. Cultures infected at MOI of 30 activated virus at a higher rate (i.e., 1–2 days faster) and degree (100%; 12/12 by day 6) in response to forskolin, than cultures infected at MOI of 3 (82%; 9/11 by day 7).

In the mock-induced QIF-PC12 control cultures, spontaneous virus production was not detected (0%; 0/11, 0/12) at either MOI. These data indicate that the efficiency of forskolin induced HSV-2 activation from QIF-PC12 cell cultures is MOI-dependent. Moreover, QIF-PC12 cell cultures established with ACV at higher MOI yielded HSV-2 sooner and from a higher proportion of cultures following induction than those established at a lower MOI. A majority of these cultures maintained HSV-2 in a quiescent state for at least 30 days and virus was inducible thereafter with forskolin.

EXAMPLE 8

ACV is Not Required for the Establishment of a Quiescent Infection With HSV-2

Since HSV-2 was found to be non-permissive in ND-PC 12 cells (data not shown), we assessed the ability of HSV-2 to establish a quiescent infection without the use of ACV. QIF-PC12 cell cultures were established with HSV-2 strain 333 in the absence of ACV in parallel to the above experiment. Cultures were cocultivated with Vera cells at a ratio of 1:1 on day 12 p.i. Nonproductive cultures were subjected to 50 μM forskolin or mock-induction on days 15 and 30 p.i. Cultures were monitored for virus production by direct plaque assay of supernatants. Virus was detected in 3/24 (12%) of cultures between day 8 p.i. and day of initial induction. Following infection, the culture media was changed daily for 3 days p.i. and thereafter every 2 to 3 days until induction.

Figure 4:
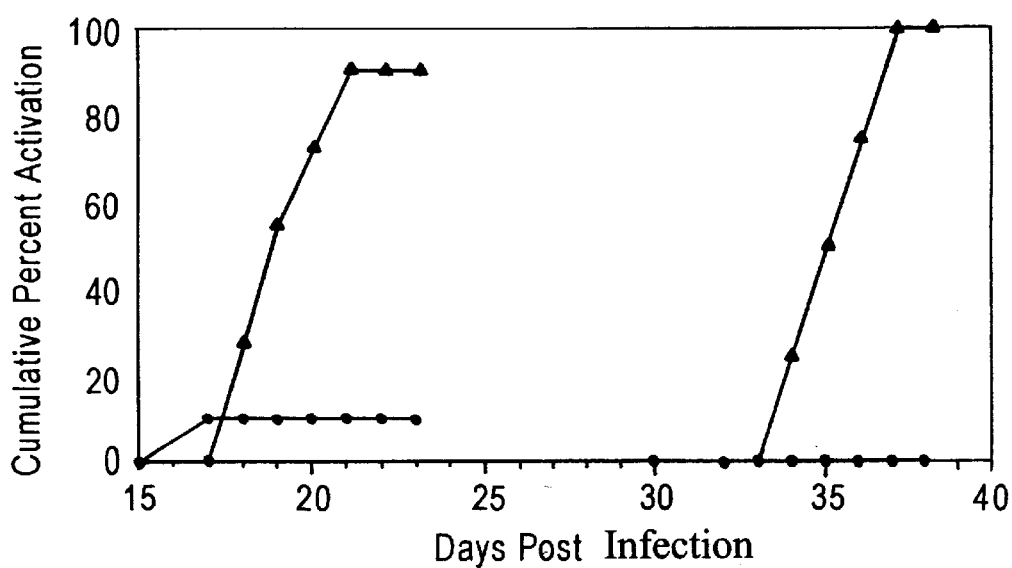
FIG. 4 shows the reactivation of HSV-2 from QIF-PC12 cell cultures established without ACV. Nonproductive cultures subjected to 50 $\mu$M forskolin (▲) or mock-induction (●) on days 15 and 30 p.i.

The majority of cultures maintained quiescence at MCI of 3 (88%, 21/24) and 30 (79%, 19/24) until the day of induction (day 15 p.i.). FIG. 4 shows that HSV-2 was produced from 91% (10/11) of forskolin induced and 10% (1/10) of mock induced cultures established at MCI of 3 by day 6 post-induction. Parallel cultures established at MCI of 30 demonstrated a similar level of forskolin induced reactivation (90%, 9/10) and slightly higher (22%, 2/9) spontaneous virus production than cultures established at MOI of 3 (data not shown). In addition, the mock induced MOI of 3 cultures that were non-productive on day 23 were maintained for an additional 7 days, and on day 30 p.i. were mock or forskolin induced. Virus was recovered from 100% (4/4) of forskolin induced cultures and 0% (0/4) of mock induced cultures. These data indicate that HSV-2 can establish a long-term (i.e., 30 days) quiescent state in ND-PC12 cell cultures without the use of ACV, and virus reactivation results from forskolin induction.

REFERENCES

Al-Saadi S A, Gross P, Wildy P (1988). Herpes simplex virus type 2 latency in the footpad of mice: effect of acycloguanosine on the recovery of virus. *J Gen Virol* 69: 433–438.

Benedetti J, Corey L, Ashley R (1994). Recurrence rates in genital herpes after symptomatic first-episode infection. *Ann Intern Med* 121: 847–854.

Block T, Barney S, Masonis J. Maggioncalda J, Valyi-Nagy T. Fraser N W (1994). Long term herpes simplex virus type 1 infection of nerve growth factor-treated PC12 cells. *J Gen Virol* 75: 2481–2487.

Bourne N, Stanberry L R. Connelly B L, Kurawadwala J, Straus S E, Krause P R (1994). Quantity of latency-associated transcript produced by herpes simplex virus is not predictive of the frequency of experimental recurrent genital herpes. *J Infect Dis* 169: 1084–1087.

Colberg-Poley A M, Isom H C, Rapp F (1979. Reactivation of herpes simplex virus type 2 from a quiescent state by human cytomegalovirus. *Proc Nat Acad Sci USA* 76: 5948–5951.

Colberg-Poley A M, Isom H C, Rapp F (1981). Involvement of an early human cytomegalovirus function in reactivation of quiescent herpes simplex virus type 2. *J Viral* 37: 1051–1059.

Croen K D, Ostrove J M, Dragovic L, Straus E (1991). Characterization of herpes simplex virus type 2 latency-associated transcription in human sacral ganglia and in cell culture. *J Infect Dis* 163: 23–28.

Danaher R J, Jacob R J, Miller C S (1999a). Establishment of a quiescent herpes simplex virus type 1 infection in neurally-differentiated PC12 cells. *J Neuro Virol* 5: 258–267.

Danaher R J, Jacob R J, Chorak M D, Freeman C S, Miller C S (1999b). Heat stress induces reactivation of herpes simplex virus type 1 from quiescently infected neurally-differentiated PC12 cells. *J Neuro Virol* 5: 374–383.

Dolan A, Jamieson F E, Cunningham C, Barnett B C, McGeoch D J (1998). The genome sequence of herpes simplex virus type 2. *J Virol* 72: 2010–2021.

Hammer S M, Richter B S, Hirsch M S (1981). Activation and suppression of herpes simplex virus in a human T lymphoid cell line. *J Immunol* 127:144–148.

Harris R A, Everett R D, Zhu X, Silverstein S, Preston C M. (1989). The HSV immediate early protein VMV 110 reactivates latent HSV type 2 in an in vitro latency system. *J Virol* 63:3513–3515.

Harris R A, Preston C M (1991). Establishment of latency in vitro by the herpes simplex virus type 1 mutant in 1814. *J Gen Virol* 72:907–913.

Hill T J, Field H J, Roome A P C (1972). Intraxonal location of herpes simplex virus particles. *J Gen Virol* 15:253–257.

Kieff E D, Bachenheimer S L, Roizman B (1971). Size, composition, and structure of the deoxyribonucleic acid of herpes simplex virus subtypes 1 and 2. *J Virol* 8:125–132.

Kieff E, Hoyer B, Bachenheimer S. Roizman B (1972). Genetic relatedness of type 1 and type 2 herpes simplex viruses. *J Virol* 9:738–745.

Kondo Y, Yura Y, Iga H, Yanagawa T, Yoshida H. Furumoto N, Sato M (1990). Effect of hexamethylene bisacetamide and cyclosporin A on recovery of herpes simplex virus type 2 from the in vitro model of latency in a human neuroblastoma cell line. *Cancer Res* 50:7852–7857.

Krause P R, Stanberry L R, Bourne N, Connelly B, Kurawadwala J F, Patel A, Straus S E (1995). Expression of the herpes simplex virus type 2 latency-associated transcript enhances spontaneous reactivation of genital herpes in latently infected guinea pigs. *J Exp Med* 181:297–306.

Kurata T, Kurata K, Aoyama K (1978). Reactivation of herpes simplex virus (type 2) infection in trigeminal ganglia and oral lips with cyclophosphamide treatment. *Jpn J Exp Med* 48:427–435.

MacLean A, Robertson L, McKay E, Brown S M (1991). The RL neurovirulence locus in herpes simplex virus type 2 strain HG52 plays no role in latency. *J Gen Virol* 72:2305–2310.

Martin J R, Suzuki S (1989). Targets of infection in a herpes simplex-reactivation model. *Acta Neuropathol (Berl)* 77:402–411.

Miller C S, Smith K O (1991). Enhanced replication of herpes simplex virus type 1 in human cells. *J Dent Res* 70:111–117.

Mitchell W J, Deshmane S L, Dolan A, MeGeoch D J, Fraser N W (1990). Characterization of herpes simplex virus type 2 transcription during latent infection of mouse trigeminal ganglia. *J Virol* 64: 5342–5348.

O'Neill F (1977). Prolongation of herpes simplex virus latency in cultured human cells by temperature elevation. *J Virol* 24:41–46.

O'Neill F J, Goldberg R J, Rapp F (1972). Herpes simplex virus latency in cultured human cells following treatment with cytosine arabinoside. *J Gen Virol* 14:189–197.

Russell J, Stow N D, Stow E C, Preston C M (1987). Herpes simplex virus genes involved in latency in vitro. *J Gen Virol* 68:3009–3018.

Russell J. Preston C M (1986). An in vitro latency system for herpes simplex virus type 2. *J Gen Virol* 67:397–403.

Scheck A C, Wigdahl B, Rapp F (1989). Transcriptional activity of the herpes simplex virus genome during establishment, maintenance, and reactivation of in vitro virus latency. *Intervirology* 30:121–136.

Stanberry L R, Kern E R, Richards J T, Abbott T M, Overall Jr J C (1982). Genital herpes in guinea pigs: pathogenesis of the primary infection and description of recurrent disease. *J Infect Dis* 146:397–404.

Stephanopoulos D E, Kappes J C, Bernstein D I. (1988). Enhanced in vitro reactivation of herpes simplex virus type 2 from latently infected guinea-pig neural tissues by 5-azacytidine. *J Gen Virol* 69:1079–1083.

Stevens J G, Cook M L (1971). Latent herpes simplex virus in spinal ganglia of mice. *Science* 173:843–845.

Su Y-H, Meegalla R L, Chowhan R, Cubitt C, Oakes J E, Lausch R N, Fraser N W, Block T M (1999). Human corneal cells and other fibroblasts can stimulate the appearance of herpes simplex virus from quiescently infected PC12 cells. *J Virol* 73:4171–4180.

Wang K, Pesnicak L, Straus S E (1997). Mutations in the 5' end of the herpes simplex virus type 2 latency-associated transcript (LAT) promoter affect LAT expression in vivo but not the rate of spontaneous reactivation of genital herpes. *J Virol* 71:7903–7910.

Whitley R J (1996). Herpes simplex viruses. In: *Fields Virology*. 3rd edition. Fields B N, Knipe D M, Howley P M (eds). Lippincott-Raven Publishers: Philadelphia pp 2297–2342.

Wigdahl B L, Isom H C, Rapp F (1981). Repression and activation of the genome of herpes simplex viruses in human cells. *Proc Natl Acad Sci* 78: 6522–6526.

Wigdahl B L, Scheck A C, De Clercq E, Rapp F (1982b). High efficiency latency and activation of herpes simplex virus in human cells. *Science* 217:1145–1146.

Wilcox C L, Johnson Jr E M (1988). Characterization of nerve factor-dependent herpes simplex virus latency in neurons in vitro. *J Virol* 62:393–399.

Wilcox C L, Smith R L, Freed C R, Johnson Jr E M (1990). Nerve growth factor-dependence of herpes simple virus latency in peripheral sympathetic and sensory neurons in vitro. *J Neuroscience* 10:1268–1275.

Yoshikawa T, Stanberry L R, Bourne N, Krause P R (1996). Downstream regulatory elements increase acute and latent herpes simplex virus type 2 latency-associate transcript expression but do not influence recurrence phenotype establishment of latency. *J Virol* 70 1535–1541.

Yura Y, Terashima K. Iga H, Yanagawa T, Yoshida H, Hayashi V. Sato M (1986). A latent infection of herpes simplex virus type 2 in a neuroblastoma cell line IMR-32. *Arch Virol* 90: 249–260.

What is claimed is:

1. A PC12 cell quiescently infected with a human herpes simplex 2 virus (HSV-2).

2. A method of reactivating a quiescent virus from at least one quiescently-infected PC12 cell, comprising, introducing a reactivator to a cell of claim 1.

3. A method for determining the ability of a test reagent to suppress virus reactivation from a quiescently-infected PC12 cell of claim 1, comprising:
    a) introducing a test reagent to said PC12 cell; and
    b) introducing to said PC12 cell a reactivator; and
    c) determining if reactivation has been suppressed.

4. A method for determining the ability of a test reagent to induce virus reactivation from a PC12 cell of claim 1, comprising:
    a) introducing a test reagent to said PC12 cell; and
    b) determining if reactivation has been induced.

5. A method for eliciting phenotypic change in a PC12 cell of claim 1, introducing a reactivator to said PC12 cell, and eliciting a phenotypic change in said PC12 cell.

6. The method of claim 5 wherein said phenotypic change is selected from the group consisting of synthesis of myelin, synthesis of neurotransmitter, cell death, and viral shedding.

7. A method to identify nucleic acid molecules and/or proteins involved in virus reactivation, comprising:
    a) reactivating a PC12 cell of claim 1 with a reactivator; and
    b) identifying nucleic acid molecules and/or proteins which are uniquely expressed during reactivation.

8. A method to identify the origins of DNA replication important to virus reactivation, comprising:
    a) reactivating a PC12 cell of claim 1 with a reactivator; and
    b) identifying the origins of replication which are uniquely associated with reactivation.

9. A method to screen a quiescent virus relative ability to be reactivated, comprising:
    a) introducing a reactivator to a PC12 cell of claim 1; and
    b) determining the relative magnitude of reactivation.

10. A method to determine a reagent's ability to inhibit establishment of a quiescent viral infection, comprising:
    a) introducing an HSV-2 virus to differentiated and viable PC12 cells in a serum-free, test reagent-containing medium;
    b) replenishing the medium after introducing the virus to maintain acceptable cell viability; and
    c) determining if reagent inhibited establishment of quiescence.

11. A method of establishing quiescently-infected PC12 cells, comprising:
    a) introducing a HSV-2 virus to neurally-differentiated and viable PC12 cells in a serum-free medium, said differentiated PC12 cells being in a container; and
    b) incubating said container with an antiviral reagent for a time necessary to accomplish quiescence of viral activity; and
    c) removing said antiviral agent from said container.

12. The method of claim 11, wherein the antiviral reagent is selected from the group consisting of acycloguanosine (acyclovir), zidovudine (AZT), lamivudine (3TC), indinavir (IDV), ganciclovir, famciclovir, foscarnet, idoxyuridine, phosphoacetic acid, 5-fluorouracil, and analogs thereof.

13. The method of claim 12, wherein said container is incubated with acycloguanosine for approximately five (5) to twelve (12) days.

14. The method of claim 13, wherein said container is incubated at a temperature less than 40 degrees Celsius (40° C.).

15. The method of claim 11, wherein said serum-free medium allows for constant cell density and imparts neural characteristics to said cells.

16. A method of establishing quiescently-infected PC12 cells, comprising:
    a) introducing an HSV-2 virus to neurally-differentiated and viable PC12 cells in a serum-free medium; and
    b) replenishing the serum-free medium after introducing the virus to maintain acceptable cell viability.

17. A method of claim 16 wherein the medium is replenished daily for 3 days and thereafter every two (2) to three (3) days until experimentation.

18. A method to identify nucleic acid molecules and/or proteins involved in establishing virus quiescence, comprising:
   a) establishing quiescence according to claims 11 or 16; and
   b) identifying nucleic acid molecules and/or proteins which are uniquely expressed during establishment of quiescence.

19. A method to identify the origins of DNA replication important to establishing virus quiescence, comprising:
   a) establishing quiescence according to claims 11 or 16; and
   b) identifying the origins of replication which are uniquely associated with establishing quiescence.

20. A method to identify nucleic acid molecules and/or proteins involved in maintaining virus quiescence, comprising:
   a) establishing quiescence according to claims 11 or 16; and
   b) identifying nucleic acid molecules and/or proteins which are uniquely expressed during maintenance of quiescence.

21. A method to identify the origins of DNA replication important to maintaining virus quiescence, comprising:
   a) establishing quiescence according to claims 11 or 16; and
   b) identifying the origins of replication which are uniquely associated with maintaining quiescence.

22. A method of claim 21 wherein the medium is replenished daily for 3 days and thereafter every two (2) to three (3) days until experimentation.

* * * * *